US 7,572,449 B2

United States Patent
Hill et al.

(10) Patent No.: US 7,572,449 B2
(45) Date of Patent: Aug. 11, 2009

(54) **VACCINE AGAINST *YERSINIA* COMPRISING ONE OR TWO ANTIBODIES, ONE SPECIFIC FOR *YERSINIA PESTIS* F1-ANTIGEN AND THE OTHER ONE FOR *YERSINIA PESTIS* V-ANTIGEN**

(75) Inventors: James Hill, Salisbury (GB); Ethel Diane Williamson, Salisbury (GB); Richard William Titball, Salisbury (GE)

(73) Assignee: The Secretary of State for Defense in Her Britannic Majesty's Government of the United Kingdom of Great Britain and Northern Ireland (GB)

( * ) Notice: Subject to any disclaimer, the term of this patent is extended or adjusted under 35 U.S.C. 154(b) by 209 days.

(21) Appl. No.: 10/525,057

(22) PCT Filed: Aug. 29, 2003

(86) PCT No.: PCT/GB03/03747

§ 371 (c)(1),
(2), (4) Date: Sep. 14, 2005

(87) PCT Pub. No.: WO2004/019980

PCT Pub. Date: Mar. 11, 2004

(65) Prior Publication Data

US 2006/0093609 A1 May 4, 2006

(30) Foreign Application Priority Data

Aug. 31, 2002 (GB) ................................. 0220257.0

(51) Int. Cl.
*A61K 39/40* (2006.01)
(52) U.S. Cl. ............... 424/164.1; 424/139.1; 424/150.1
(58) Field of Classification Search ....................... None
See application file for complete search history.

(56) References Cited

U.S. PATENT DOCUMENTS 6,248,329 B1 * 6/2001 Chandrashekar et al. . 424/191.1

FOREIGN PATENT DOCUMENTS

| WO | WO 95/18231 | 7/1995 |
| WO | WO 96/28551 | 9/1996 |
| WO | WO 00/73347 | 12/2000 |
| WO | WO 01/70200 A1 | 9/2001 |

OTHER PUBLICATIONS

Motin et al. (Infect. Immun., 62:4192-4201, 1994).*
Greenspan et al. (Nature Biotechnology 17: 936-937, 1999).*
Ellis (Chapter 29 of Vaccines, Plotkin, et al. (eds) WB Saunders, Philadelphia, 1988.*
Bowie et al (Science, 1990, 247:1306-1310).*
Anderson, et al., 'Protection of Mice from Fatal Bubonic and Pneumonic Plague by Passive Immunization with Monoclonal Antibodies Against the F1 Protein of *Yersinia pestis*,' *Am. J. Trop. Med. Hyg.*, 56(4):471-473 (1997).
Anderson, et al., 'Protection of Mice from Fatal Bubonic and Pneumonic Plague by Passive Immunization with Monoclonal Antibodies Against the F1 Protein of *Yersinia pestis*,' *Am. J. Trop. Med. Hyg.*, 56(4):471-473 (1997).
Casadevall, 'Short Analytical Review Passive Antibody Therapies: Progress and Continuing Challenges,' *Clinical Immunology*, 93(1):5-15 (1999).
Cornelis, 'Minireview The *Yersinia* Deadly Kiss,' *Journal of Bacteriology*, 180(21):5495-5504 (1998).
de Haard, et al., 'A Large Non-Immunized Human Fab Fragment Phage Library That Permits Rapid Isolation and Kinetic Analysis of High Affinity Antibodies,' *Journal of Biological Chemistry*, 274(26):18218-18230 (1999).
Du, et al., 'Role of Fraction 1 Antigen of *Yersinia pestis* in Inhibition of Phagocytosis,' *Infection and Immunity*, 70(3):1453-1460 (2002).
Duplantier, et al., 'Resurgence de la peste dans le district d'Ikongo a Maagascar en 1998,' *Bulletin De La Societe De Pathologie Exotique*, 94(2):119-112 (2001).
Fields, et al., Virulence role of V antigen of *Yersinia pestis* at the bacterial surface, *Infection and Immunity*, 67(10):5395-5408 (1999).
Frank, et al., 'Generation and Characterization of a Protective Monoclonal Antibody to *Pseudomonas aeruginosa* PcrV,' *Journal of Infectious Diseases*, 186:64-73 (2002).
Green, et al., 'The SCID/Beige mouse as a model to investigate protection against *Yersinia pestis*,' *FEMS Immunology and Medical Microbiology*, 23(2):107-113 (1999).
Guiyoule, et al., 'Recent Emergence of New Variants of *Yersinia pestis* in Madagascar,' *Journal of Clinical Microbiology*, 35(11):2826-2833 (1997).
Guiyoule, et al., 'Transferable Plasmid-Mediated Resistance to Streptomycin in a Clinical Isolate of *Yersinia pestis*,' *Emerging Infectious Diseases*, 7(1):43-48 (2001).

(Continued)

*Primary Examiner*—Robert B Mondesi
*Assistant Examiner*—Brian J Gangle
(74) *Attorney, Agent, or Firm*—Kilpatrick Stockton LLP

(57) ABSTRACT

The use of (i) an antibody specific for *Yersinia pestis* F1-antigen, or a binding fragment thereof, or (ii) an antibody specific for *Yersinia pestis* V-antigen, or a binding fragment thereof, or a combination of (i) and (ii), in the production of a medicament for the treatment of infection by *Yersinia pestis*. It has been found that such treatments are effective therapies for *Yersinia pestis* infection. In addition, the combination produces a synergistic effect when used prophylactically.

8 Claims, No Drawings

OTHER PUBLICATIONS

Heath, et al., 'Protection against experimental bubonic and pneumonic plague by a recombinant capsulat F1-V antigen fusion protein vaccine,' *Vaccine*, 16(11/12):1131-1137 (1998).

Hill, et al., 'Synergistic protection of mice against plague with monoclonal antibodies specific for the F1 and V antigens of *Yersinia pestis*,' *Infection and Immunity*, 71(4):2234-2238 (2003).

Hill, et al., 'Regions of *Yersinia pestis* V Antigen That contribute to Protection against Plague Identified by Passive and Active Immunization,' *Infection and Immunity*, 65(11):4476-4482 (1997).

Hueck, 'Type III Protein Secretion Systems in Bacterial Pathogens of Animals and Plants,' *Microbiology and Molecular Biology Reviews*, 62(2):379-433 (1998).

Jones, et al., 'Protective efficacy of a fully recombinant plague vaccine in the guinea pig,' *Vaccine*, 21:3912-3918 (2003).

Jones, et al., 'Protection conferred by a fully recombinant sub-unit vaccine against *Yersinia pestis* in male and female mice of four inbred strains,' *Vaccine*, 19:358-366 (2001).

Keller, et al., 'Passive Immunity in Prevention and Treatment of Infectious Diseases,' *Clin. Microbiol. Rev.*, 13(4):602-614 (2000).

Knappik, et al., 'Fully Synthetic Human Combinatorial Antibody Libraries (HuCAL) Based on Modular Consensus Frameworks and CDRs Randomized with Trinucleotides,' *Journal of Molecular Biology*, 296:57-86 (2000).

Leary, et al., 'Active Immunization with Recombinant V Antigen from *Yersinia pestis* Protects Mice against Plague,' *Infection and Immunity*, 63(8):2854-2858 (1995).

Leary, et al., 'Expression of an F1/V fusion protein in attenuated *Salmonella typhimurium* and protection of mice against plague,' *Microbial Pathogenesis*, 23:167-179 (1997).

Mayers, et al., 'Antitoxin therapy for botulinum intoxication,' *Reviews in Medical Microbiology*, 12(1):29-37 (2001).

Migliani, et al., 'Resurgence de la peste dans le district d'Ikongo a Madagascar en 1998,' *Bulletin De La Societe De Pathologie Exotique*, 94(2):115-118 (2001).

Motin, et al., 'Suppression of Mouse Skin Allograft Rejection by Protein A-*Yersiniae* V Antigen Fusion Peptide,' *Transplantation*, 63(7):1040-1042 (1997).

Motin, et al., 'Passive Immunity to *Yersiniae* Mediated by Anti-Recombinant V Antigen and Protein A-V Antigen Fusion Peptide,' *Infection and Immunity*, 62(10):4192-4201 (1994).

Nakajima, et al., 'Suppression of Cytokines in Mice by Protein A-V Antigen Fusion Peptide and Restoration of Synthesis by Active Immunization,' *Infection and Immunity*, 63(8):3021-3029 (1995).

Neuberger, et al., 'Mice perform a human repertoire,' *Nature*, 386:25-26 (1997).

Nissim, et al., 'Antibody fragments from a 'single pot' phage display library as immunochemical reagents,' *Embo Journal*, 13(3):692-698 (1994).

Perry, et al., '*Yersinia pestis*—Etiologic Agent of Plague,' *Clinical Microbiology Reviews*, 10(1):35-66 (1997).

Pettersson, et al., 'The V-antigen of *Yersinia* is surface exposed before target cell contact and involved in virulence protein translocation,' *Molecular Microbiology*, 32(5):961-976 (1999).

Ratsitorahina, et al., 'Epidemiological and diagnostic aspects of the outbreak of pneumonic plague in Madagascar,' *Lancet*, 355:111-113 (2000).

Rosqvist, et al., 'Intracellular Targeting of the *Yersinia* YopE Cytotoxin in Mammalian Cells Unduces Actin Microfilament Disruption,' *Infection and Immunity*, 59(12):4562-4569 (1991).

Rosqvist, et al., 'Target cell contact triggers expression and polarized transfer of *Yersinia* YopE cytotoxin into mammalian cells,' *Embo Journal*, 13(4):964-972 (1994).

Russell, et al., 'A comparison of Plague vaccine, USP and EV76 vaccine induced protection against *Yersinia pestis* in a murine model,' *Vaccine*, 13(16):1551-1556 (1995).

Sawa, et al., 'Active and passive immunization with the *Pseudomonas* V antigen protects against type III intoxication and lung injury,' *Nature Medicine*, 5(4):392-398 (1999).

Shime, et al., 'Therapeutic Administration of Anti-PcrV F(ab')$_2$ in Sepsis Associated with *Pseudomonas aeruginosa*,' *Journal of Immunology*, 167:5880-5886 (2001).

Sing, et al., '*Yersinia enterocolitica* Evasion of the Host Innate Immune Response by V Antigen-Induced IL-10 Production of Macrophases Is Abrogated in IL-10-Deficient Mice,' *Journal of Immunology*, 168:1315-1321 (2002).

Shivaji, et al., 'Identification of *Yersnia pestis* as the causative organism of plague in India as determined by 16S rDNA sequencing and RAPD-based genomic fingerprinting,' *FEMS Microbiology Letters*, 189:247-252 (2000).

Taylor, et al., 'Humanised monoclonal antibody to respiratory syncytial virus,' *Lancet*, 337:1411-1412 (1991).

Titball, et al., 'Expression of the *Yersinia pestis* Capsular Antigen (F1 Antigen) on the Surface of an aroA Mutant of *Salmonella typhimurium* Induces High Levels of Protection against Plague,' *Infection and Immunity*, 65(5):1926-1930 (1997).

Titball, et al., 'Vaccination against bubonic and pneumonic plague,' *Vaccine*, 19:4175-4184 (2001).

Weeks, et al., 'Anti-V antigen antibody protects macrophages from *Yersinia pestis*-induced cell death and promotes phagocytosis,' *Microbial Pathogenesis*, 32:227-237 (2002).

Welkos, et al., 'V antigen of *Yersinia pestis* inhibits neutrophil chemotaxis,' *Microbial Pathogenesis*, 24:185-196 (1998).

Williamson, et al., 'A sub-unit vaccine elicits lgG in serum, spleen cell cultures and bronchial washings and protects immunized animals against pneumonic plague,' *Vaccine*, 15(10):1079-1084 (1997).

Williamson, et al., 'An IgG1 titre to the F1 and V antigens correlates with protection against plague in the mouse model,' *Clinical and Experimental Immunology*, 116:107-114 (1999).

Williamson, et al., 'Plague vaccine research and development,' *Journal of Applied Microbiology*, 91:606-608 (2001).

Williamson, et al., 'A single dose sub-unit vaccine protects against pneumonic plague,' *Vaccine*, 19:566-571 (2000).

Williamson, et al., 'A new improved sub-unit vaccine for plague: the basis of protection,' *FEMS Immunology and Medical Microbiology*, 12:223-230 (1995).

Winter, et al., 'Antibody-based therapy Humanized antibodies,' *Trends in Pharmacological Sciences*, 14:139-143 (1993).

Chapter 25.2 in vol. 5 of Comprehensive Medicinal Chemistry "Formulation," vol. 5, pp. 567-591 (Corwin Hansch; Chairman of Editorial Board, Pergamon Press) (1990).

\* cited by examiner

VACCINE AGAINST *YERSINIA* COMPRISING ONE OR TWO ANTIBODIES, ONE SPECIFIC FOR *YERSINIA PESTIS* F1-ANTIGEN AND THE OTHER ONE FOR *YERSINIA PESTIS* V-ANTIGEN

CROSS REFERENCE TO RELATED APPLICATIONS

This application is the U.S. national phase of International Application No. PCT/GB2003/003747 filed on Aug. 29, 2003 and published in English on Mar. 11, 2004 as International Publication No. WO 2004/019980 A1, which application claims priority to Great Britain Application No. 0220257.0 filed on Aug. 31, 2002, the contents of which are incorporated by reference herein.

The present invention relates to antibodies, which are administered to a human or animal prophylactically or as a therapy.

In particular, the present invention relates to antibodies, which act synergistically when administered prophylactically and when administered as a therapy.

The present invention also relates to novel vaccines and the protection and treatment against the organism *Yersinia pestis*. Such vaccines are capable of offering protection against bubonic and pneumonic plague.

*Yersinia pestis*, the causative agent of plague, has accounted for the deaths of millions of people throughout recorded history. The second pandemic (The Black Death) is thought to have killed an estimated 17 million to 28 million Europeans between the $14^{th}$ and $17^{th}$ centuries. The third pandemic, believed to have started in the Yunan Province of China in the 1850s, has lead to the worldwide spread of plague, which is now endemic to several regions including Africa, India and the South Western states of the USA (Perry, R. D. et al. 1997. Clinical Microbiology Reviews 10:35-66). Despite the current low incidence of plague, the bacterium resides in natural animal reservoirs and regular, though relatively small outbreaks of plague occur (Duplantier, J. M. et al. 2001. Bulletin De La Societe De Pathologie Exotique 94:119-122; Migliani, R. et al. 2001. Bulletin De La Societe De Pathologie Exotique 94:115-118; Ratsitorahina, M. et al. 2000. Lancet 355:111-113).

Improvements in transport links between endemic areas and large population centres bring with it the potential for large-scale plague outbreaks, highlighted by the recent outbreak in India (Shivaji, S. et al. 2000. Fems Microbiology Letters 189:247-252). There is therefore a need for effective disease surveillance to reduce the risk of plague transmission to new areas and subsequent outbreaks of disease.

Vaccination is recommended for research scientists and other professionals who come into contact with the bacterium, but fast-acting treatments are also required for individuals exposed to *Y. pestis* in endemic areas, or through their work. In addition, after a major outbreak there would be a need to protect healthcare workers and first-responders.

At present protection against plague can be mediated through vaccination or antibiotic treatment. Antibiotics, including streptomycin and tetracycline, are used both to treat plague victims and as prophylaxis to control the spread of the disease (Perry, R. D. et al. 1997. Clinical Microbiology Reviews 10:35-66). The incidence of antibiotic resistance in *Y. pestis* is low but recent plague isolates in Madagascar have been found to have multiple drug resistance, conferred by a transferable plasmid (Guiyoule, A. G. et al. 2001. Emerging Infectious Diseases 7:43-48; Guiyoule, A. et al. 1997. Journal of Clinical Microbiology 35:2826-2833). Existing plague vaccines include killed whole-cell preparations and efforts to develop new vaccines are in progress (Williamson, E. D. 2001. Journal of Applied Microbiology 91:606-608).

Problems associated with whole-cell vaccines include relatively low levels of protection, adverse side-effects, slow time-to-immunity, and a need for regular booster immunisations (Russell, P et al. 1995. Vaccine 13:1551-1556). Although whole cell vaccines are thought to be effective against the most common form of plague (bubonic plague), that develops following a bite from an infected insect, their efficacy against pneumonic plague has been questioned.

Next-generation plague sub-unit vaccines are being developed, based on the recombinant F1-antigen (F1) and low calcium response V-antigen (LcrV) proteins, derived from *Y. pestis*. Immunisation with either protein provides protection against pneumonic or bubonic disease in animal models of infection (Heath, D. G. et al. 1998. Vaccine 16:1131-1137; Leary, S. E. C. et al. 1995. Infection and Immunity 63:2854-2858; Williamson, E. D. 2001. Journal of Applied Microbiology 91:606-608) but greater than additive protection is achieved when F1 and LcrV are combined, with protection against up to $10^9$ median lethal doses (MLD) of *Y. pestis* reported (Williamson, E. D. et al. 1995. Fems Immunology and Medical Microbiology 12:223-230). Such vaccines must be administered prior to exposure, and multiple doses are required. Although strategies to reduce the time to immunity and the number of vaccine doses have shown promise (Williamson, E. D. et al. 2000. A single dose sub-unit vaccine protects against pneumonic plague. Vaccine 19:566-571), it is unlikely that vaccination will provide post-exposure protection against disease.

There is therefore a need for fast-acting anti-plague treatments to provide rapid therapy, particularly in the event that drug resistant strains of *Y. pestis* are involved.

Previously, F1-04-A-G1, a mouse monoclonal antibody raised against F1 was shown to protect mice in models for bubonic and pneumonic plague (Anderson, G. W. et al. 1997. American Journal of Tropical Medicine and Hygiene 56:471-473). Also, preliminary studies showed that an LcrV-specific monoclonal antibody (Mab 7.3) protected mice in a bubonic plague model (Hill, J. et al. 1997. Infection and Immunity 65:4476-4482).

Although antisera have been used to treat a range of diseases caused by other pathogens (Keller M. A. et al. 2000. Clin. Microbiol. Rev. 2000 13:602-14), neither antisera nor monoclonal antibodies have been previously proposed as a treatment for plague. The applicants have found however, that antibody therapy is effective in treating plague infections, and that combinations of antibodies can operate synergistically in providing protection against infection.

According to the present invention there is provided the use of (i) an antibody specific for *Yersinia pestis* F1-antigen, or a binding fragment thereof, or (ii) an antibody specific for *Yersinia pestis* V-antigen, or a binding fragment thereof, or a combination of (i) and (ii), in the production of a medicament for the treatment of infection by *Yersinia pestis*.

As used herein the term "binding fragment" refers to fragments of antibodies such as F(ab) and F(ab') fragments, or single chain antibodies, which bind to the target antigen.

In particular, the medicament will comprise a combination of (i) and (ii) is used. Preferably the combination comprises at least one antibody specific for *Yersinia pestis* F1-antigen, and at least one antibody specific for *Yersinia pestis* V-antigen.

If desired, more than one antibody specific for different epitopes within the F1-antigen and/or V-antigen, can be employed.

Suitably the antibodies used are monoclonal antibodies or binding fragments thereof, but in particular are monoclonal antibodies.

In particular, the antibody specific for *Yersinia pestis* V-antigen or binding fragment thereof specifically binds an epitope of the V-antigen found between amino acids 1 and 275 and preferably an epitope found between amino acids 135-275 of the sequence of the V-antigen as shown for instance in WO 96/28551 that issued as U.S. Pat. No. 5,985, 285 on Nov. 16, 1999. Passive transfer of LcrV-specific polyclonal antiserum protected mince against plague and that protective epitopes were assigned to region 168-275 (Motin, V. L. et al. 1994. Infection and Immunity 62:4192-4201). Similarly, Mab 7.3 used in the present application has been mapped to bind to a conformational epitope between aa 135-275 of LcrV (Hill, J. et al. 1997. Infection and Immunity 65:4476-4482). Therefore, this central region of LcrV appears to be a good target for antibodies useful in the present invention.

Suitably the medicament is for administration up to about 48 hours post-infection, although longer periods may be envisaged if the dosage is increased sufficiently.

A number of strategies can be used to increase the clinical acceptability of the antibodies or binding fragments (Casadevall, A. 1999. Clinical Immunology 93:5-15). For example, the specificity of animal antibodies can be transferred to a human antibody framework, a process termed "humanisation" (Taylor, G. et al. 1991. Lancet 337:1411-1412; Winter, G. et al. 1993. Trends in Pharmacological Sciences 14:139-143) or animal antibodies can be chemically treated to improve their therapeutic properties (Mayers, C. N. et al. 2001. Reviews in Medical Microbiology 12:29-37). Alternatively, antibodies can be generated from naive human single chain antibody libraries (de Haard, H. J. et al. 1999. Journal of Biological Chemistry 274:18218-18230; Knappik, A. et al. 2000. Journal of Molecular Biology 296:57-86; Nissim, A. et al. 1994. Embo Journal 13:692-698) or from immunised transgenic animals that express a human antibody repertoire (Neuberger, M. et al. 1997. Nature 386:25-26).

In a particularly preferred embodiment, the antibodies or binding fragments thereof used are "humanised" by humanization as described above, or are fully human antibodies as a result of generation from human libraries, or transgenic animals, also as described above.

The applicants have demonstrated that monoclonal antibodies specific for *Y. pestis* surface proteins can be used as a therapy for the treatment of plague. Mabs 7.3 and F1-04-A-G1 were more effective as a therapy when combined than as a single treatment, providing significant protection when administered up to 2 days after s.c. *Y. pestis* challenge.

In a further aspect, the invention provides a method of treating a human or animal suffering from the effects of infection with *Yersinia pestis*, said method comprising administering to the human or animal, a therapeutically effective amount of (i) an antibody specific for *Yersinia pestis* F1-antigen, or a binding fragment thereof, or (ii) an antibody specific for *Yersinia pestis* V-antigen, or a binding fragment thereof, or a combination of (i) and (ii), and in particular a combination of (i) and (ii) as described above.

Suitably the treatment is administered within 48 hours, and preferably within 24 hours of exposure to the infective *Yersinia pestis* organism.

The antibodies are suitably administered in the form or a pharmaceutical composition, which suitably includes a pharmaceutically acceptable carrier. Suitable carriers include solid or liquid carriers, such as saline, as are known in the art.

The compositions of the invention may be in a form suitable for oral use (for example as tablets, lozenges, hard or soft capsules, aqueous or oily suspensions, emulsions, dispersible powders or granules, syrups or elixirs), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing.

The compositions of the invention may be obtained by conventional procedures using conventional pharmaceutical excipients, well known in the art.

For example, the pharmaceutical compositions may be in the form of a sterile injectable aqueous or oily suspension, which may be formulated according to known procedures using one or more of the appropriate dispersing or wetting agents and suspending agents.

Compositions for administration by inhalation may be in the form of a conventional pressurized aerosol arranged to dispense the active antibody composition either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on Formulation the reader is referred to Chapter 25.2 in Volume 5 of Comprehensive Medicinal Chemistry (Corwin Hansch; Chairman of Editorial Board, Pergamon Press 1990).

The amount of active ingredient that is combined with one or more excipients to produce a single dosage form will necessarily vary depending upon the host treated and the particular route of administration. Dosage unit forms will generally contain about 1 mg to about 2 g of an active ingredient.

The size of the dose for therapeutic or prophylactic purposes of the compositions of the invention will vary according to the nature and severity of the conditions, the age and sex of the animal or patient and the route of administration, according to well known principles of medicine. Generally however, for therapeutic or prophylactic purposes, it will generally be administered so that a periodic dose in the range, for example, 0.5 mg to 75 mg per kg body weight is received.

Thus in yet a further aspect, the invention provides a pharmaceutical composition comprising an antibody specific for the *Yersinia pestis* V-antigen or a binding fragment thereof, and an antibody specific for the *Yersinia pestis* F1-antigen or a binding fragment thereof.

In particular the composition comprises an antibody specific for the *Yersinia pestis* V-antigen or a binding fragment thereof, and an antibody specific for the *Yersinia pestis* F1-antigen or a binding fragment thereof. Preferably these are antibodies, and most preferably monoclonal antibodies, which may be humanized or fully human. Preferred antibodies for inclusion in the composition are as described above.

The applicants have also found that the combination of antibodies protected mice against $10^5$ MLD s.c. challenge when administered as a pre-treatment. The data presented here mirrors observations that LcrV and F1 provide greater than additive protection when included in plague sub-unit vaccines (Williamson, E. D. et al. 1995. Fems Immunology and Medical Microbiology 12:223-230). Vaccine-mediated protection correlates with high specific polyclonal antibody titres to F1 and LcrV (Williamson, E. D. et al. 1999. Clinical and Experimental Immunology 116:107-114), which agrees with the present observation that the degree of protection was found to be proportional to the amount of protective antibody administered (Table 1 hereinafter).

Thus the pharmaceutical compositions of the invention may be used as a prophylactic vaccine for passive immunization for the protection of a human or animal against infection by *Yersinia pestis*, and these vaccines form a further aspect of the invention.

Yet a further aspect comprises a method of immunizing against infection by *Yersinia pestis* comprising administering a vaccine as described above.

In a further aspect, the invention provides the use of a combination of an antibody specific for *Yersinia pestis* F1-antigen, or a binding fragment thereof, and an antibody specific for *Yersinia pestis* V-antigen, or a binding fragment thereof, in the production of a medicament for the passive immunization of a human or animal against infection by *Yersinia pestis.*

Preferred antibody combinations are as described above in relation to the use in therapy.

LcrV has a key role in type III secretion (TTS) by the *Yersinia* spp., a process that allows the injection of a set of effector proteins directly into the cytosol of eukaryotic target cells upon intimate contact (Cornelis, G. R. 1998. Journal of Bacteriology 180:5495-5504; Hueck, C. J. 1998. Microbiology and Molecular Biology Reviews 62:379-433; Rosqvist, R. et al. 1991. Infection and Immunity 59:4562-4569; Rosqvist, R. et al. 1994. Embo Journal 13:964-972). The effector proteins (termed Yops) have a range of function that promote the killing of phagocytic host cells. Protective polyclonal antisera inhibited *Yersinia* TTS in HELA cell cytotoxicity experiments and LcrV was detected at the bacterial surface prior to contact with eukaryotic cells by confocal microscopy analysis (Pettersson, J. A. et al. 1999. Molecular Microbiology 32:961-976). A similar study showed that Mab 7.3, but not other non-protective Mabs, protected J774 macrophage-like cells against *Yersinia*-mediated killing (Weeks, S. et al. 2002. Mibrobial Pathogenesis 32:227-237). Antiserum raised against the LcrV homologue of *Pseudomonas aeruginosa* (PcrV) protected mice in a lung infection model and antiserum inhibited TTS-mediated cytotoxicity of J774 cells (Frank, D. W. et al. 2002. Journal of Infectious Diseases 186:64-73; Sawa, T. et al. 1999. Nature Medicine 5:392-398), and anti-PcrV F(ab')2 fragment provided therapeutic protection in a model for disease (Shime, N. et al. 2001. Journal of Immunology 167:5880-5886).

However, others did not show a correlation between protective LcrV-specific polyclonal antiserum in cytotoxicity assays (Fields, K. A. et al. 1999. Virulence role of V antigen of *Yersinia pestis* at the bacterial surface. Infection and Immunity 67:5395-5408). LcrV is also reported to have immunomodulatory properties (Motin, V. L. et al. 1997. Transplantation 63:1040-1042; Nakajima, R. et al. 1995. Infection and Immunity 63:3021-3029; Sing, A. et al. 2002. Journal of Immunology 168:1315-1321; Welkos, S. et al. 1998. Microbial Pathogenesis 24:185-196), so it remains a possibility that antibodies inhibit both TTS as well as the anti-inflammatory properties of *Y. pestis*, by blocking the interaction of secreted LcrV with an unidentified eukaryotic receptor.

F1 is expressed optimally at 37° C. and is thought to inhibit phagocytosis through the formation of a capsule-like structure on the bacterial surface, and is an effective plague vaccine (Andrews, G. P. et al. 1996. Infection and Immunity 64:2180-2187; Du, Y. D. et al. 2002. Infection and Immunity 70:1453-1460; Heath, D. G. et al. 1998. Vaccine 16:1131-1137; Titball, R. W. et al. 1997. Infection and Immunity 65:1926-1930). A recent report showed that an isogenic F1 plague mutant has impaired resistance to phagocytosis by J774 cells (Du, Y. D. et al. 2002. Infection and Immunity 70:1453-1460). Also, a virulence plasmid cured strain, deficient for TTS, was less resistant to phagocytosis and an additive effect was seen with the double mutant (F1-negative, plasmid cured strain). It was proposed that the TTS system and F1 capsule synthesis contribute in different ways to maintain the extracellular lifestyle of *Y. pestis* (Du, Y. D. et al. 2002. Infection and Immunity 70:1453-1460). By using the invention, both the TTS system and the F1 capsule of the organism are targeted, which might explain the high level of protection observed in the following examples. The present invention will now be described only by way of examples:

EXAMPLE 1

Preparation of Antibodies

Mab 7.3 and F1-04-A-G1 were purified by ammonium sulphate precipitation from hybridoma supernatants. An equal volume of saturated ammonium sulphate solution was added slowly to tissue culture supernatants, followed by overnight stirring at 4° C., then centrifugation at 3,000 g for 30 min. The pellets were drained and resuspended in PBS (GIBCO, UK) in 0.1 volumes of the original volume, then dialysed against three changes of PBS. Disposable Econopak columns (BioRad, UK) were packed with protein-G-sepharose beads (Sigma, UK) and antibody solution was passed through the column. The beads were washed with PBS, then antibody was eluted with 50 mM glycine (pH 3) and stored in fractions containing 150 μl Tris HCl (pH 9.1) per 3 ml of eluate. Protein fractions were analysed by SDS-PAGE on 10-15% Phastgels (Pharmacia, UK) and fractions containing antibody were dialysed against three changes of PBS. Antibody concentration was determined by BCA assay (Perbio, UK) with a BSA standard as recommended by the manufacturers. Antibody purity was assessed by SDS-PAGE analysis.

EXAMPLE 2

Biological Testing

Antibodies were tested in murine models of bubonic and pneumonic plague. Six to eight week old Balb/c mice were used (Charles River Limited, UK). Animal Experiments were performed in accordance with UK legislation relating to animal experimentation (Animals (Scientific Procedures) Act 1986.

Mice received antibody by intraperitoneal (i.p.) injection in 100 μl of PBS, prior to or after infection as indicated in Tables 1 to 3 hereinafter. *Y. pestis* strain GB, a fully virulent human isolate, with an estimated median lethal dose (MLD) of 1 colony forming unit via the s.c. route (Russell, P et al. 1995. Vaccine 13:1551-1556) was used in all challenge experiments. In the bubonic plague model mice received 10 to $10^5$ MLD resuspended in 100 μl PBS, by subcutaneous (s.c.) injection. In the pneumonic plague model mice were exposed to approximately 100 MLD of airborne bacteria, as described previously (Williamson, E. D. et al. 1997 Vaccine 15:1079-1084). Animals were checked at least twice daily and deaths recorded over a 14 day period.

Results

Mab 7.3 Protection Data

Mice were treated with purified Mab 7.3 24 hours prior to challenge with 10 MLD or 100 MLD of *Y. pestis*. As little as 3.5 μg of antibody protected mice and extended the mean time to death (TTD) of animals that died (Table 1).

TABLE 1

Dose-dependent protection against bubonic plague with purified Mab 7.3.

| Mab 7.3 (μg)* | MLD† | Survivors/group | TTD ± SEM§ |
|---|---|---|---|
| 35 | 10 | 5/6 | 4.0 |
| 10.5 | 10 | 5/6 | 6.0 |
| 3.5 | 10 | 0/6 | 8.2 ± 1.1 |
| 0.7 | 10 | 1/6 | 4.8 ± 0.5 |
| none | 10 | 0/6 | 4.8 ± 0.3 |
| 35 | 100 | 3/6 | 6.3 ± 0.8 |
| 10.5 | 100 | 3/6 | 3.8 ± 2.7 |
| 3.5 | 100 | 1/6 | 6.4 ± 1.5 |
| 0.7 | 100 | 0/6 | 5.2 ± 0.4 |
| none | 100 | 0/6 | 4.1 ± 0.3 |

*Mab 7.3 administered i.p. 24 hours before challenge
†*Y. pestis* administered by s.c. injection in 100 μl PBS
§Student's T-test: $p < 0.05$ compared with PBS control groups receiving the equivalent challenge.

Greater survival was noted in groups given 10.5 μg or 35 μg, compared with those that received 3.5 μg and 0.7 μg of Mab 7.3. The degree of protection was less in animals that received 100 MLD than those injected with 10 MLD (50% and 83% survivors respectively). Therefore, protection against plague was directly proportional to the amount of antibody administered and inversely proportional to the challenge dose.

Five mice received 50 μg Mab 7.3 in 100 μl PBS by intraperitonneal (i.p.) injection and serum levels were determined at different times by anti-LcrV-specific ELISA as described previously (Hill, J. et al. 1997. Infection and Immunity 65:4476-4482). The serum half-life of Mab 7.3 was determined as 5.6 days. The serum antibody level 28 days after dosing was calculated as 2 μg, and five immunised animals were challenged with 18 MLD *Y. pestis* on day 28-post antibody treatment. All Mab 7.3-treated animals survived, whereas 6 of 6 untreated mice died. This experiment demonstrated the potential for a single dose of antibody as a long-lasting prophylactic.

Mab 7.3 was administered −4 hours, +24 hours, +48 hours, or +96 hours relative to s.c. *Y. pestis* challenge. Protection was observed when antibody was given up to 48 hours post-infection. Also, a delayed time to death was observed in the +96 hours treatment group. One of +96 hours treatment group had died prior to antibody administration and the remainder displayed signs of plague indistinguishable from untreated control animals, suggesting that even when symptoms of plague are apparent antibody therapy can delay death. Mice were treated with Mab 7.3 at −4 hours, +24 hours, +48 hours or +60 hours relative to aerosol infection. Protection was seen in groups that received antibody 24 hours and 48 hours after challenge. All mice treated at +60 hours died, but a statistically significant delay in the TTD was observed, compared with untreated animals.

Combined F1-04-A-G1 and Mab 7.3 Treatment

F1-04-A-G1, administered singly or in combination with Mab 7.3 prior to aerosol challenge, protected mice against plague (Table 2).

TABLE 2

F1-04-A-G1 and Mab 7.3 protect against aerosol plague challenge.

| Antibody treatment* | Aerosol challenge dose (MLD) | Survivors per group† |
|---|---|---|
| PBS | 100 | 0/10 |
| F1-04-A-G1 | 100 | 9/10 |
| Mab 7.3 | 100 | 10/10 |
| F1-04-A-G1 + Mab 7.3 | 100 | 9/10 |

*35 μg of Mab 7.3 and/or 100 μg of F1-04-A-G administered by i.p. injection in 100 μg PBS, 4 hours prior to challenge.
†Deaths recorded over a 14 day period This confirmed the prophylactic properties of F1-04-A-G1 in the pneumonic plague model (Anderson, G. W. et al. 1997. American Journal of Tropical Medicine and Hygiene 56:471-473). Mab 7.3 was less effective as a treatment against s.c. *Y. pestis* challenge than aerosol challenge, therefore the bubonic plague model chosen for further co-administration studies to test for antibody synergy.

First, antibodies were tested as a pre-treatment against challenge with 50 to $10^5$ MLD of *Y. pestis* G5 (Table 3).

TABLE 3

Enhanced protection with F1-04-A-G1 and Mab 7.3 as a pre-treatment.

| Antibody treatment* | *Y. pestis* challenge (MLD)† | Survivors per group |
|---|---|---|
| untreated | 50 | 0/6 |
| F1-04-A-G1 + Mab 7.3 | $10^2$ | 6/6 |
| F1-04-A-G1 + Mab 7.3 | $10^3$ | 6/6 |
| F1-04-A-G1 + Mab 7.3 | $10^4$ | 5/6 |
| F1-04-A-G1 + Mab 7.3 | $10^5$ | 6/6 |

*mice were immunised i.p. with 35 μg Mab 7.3 and 100 μg F1-04-A-G1 in PBS.
†s.c plague challenge 4 hours after antibody administration Surprisingly, protection was observed at all challenge doses; breakthrough was expected at challenge doses greater than 100 MLD (see Table 1 and Anderson, G. W. et al. 1997. American Journal of Tropical Medicine and Hygiene 56:471-473). Next the combined antibody treatment was tested as a plague therapy. Mice that received the antibody cocktail 48 hours after challenge were protected better than animals that received single antibody therapy. The data indicates that Mab 7.3 and F1-04-A-G1 act synergistically as a pre-treatment and as a therapeutic in our plague models.

The invention claimed is:

1. A method of treating a human or animal suffering from effects of infection with *Yersinia pestis*, comprising administering to the human or the animal a therapeutically effective amount of a medicament comprising an antibody specific for *Yersinia pestis* F1-antigen or a binding fragment thereof, and an antibody specific for *Yersinia pestis* V-antigen or a binding fragment thereof.

2. The method of claim 1, wherein the antibodies are monoclonal antibodies.

3. The method of claim 1, wherein the medicament is for administration up to about 48 hours post-infection.

4. The method of claim 1, wherein the antibody specific for *Yersinia pestis* V-antigen or the binding fragment thereof specifically binds an epitope of the V-antigen found between amino acids 135-275 of sequence of the V-antigen.

5. The method of claim 1, wherein the antibodies or the binding fragments thereof, are humanized.

6. The method of claim 1, wherein the method comprises administering a combination of the antibody specific for *Yersinia pestis* F1-antigen and the antibody specific for *Yersinia pestis* V-antigen.

7. The method of claim 1, wherein the antibody specific for *Yersinia pestis* V-antigen or the binding fragment thereof specifically binds an epitope of the V-antigen found between amino acids 1-275 of sequence of the V-antigen.

8. The method of claim 1, wherein the medicament is administered in a form suitable for oral use, for administration by inhalation, for administration by insufflation or for parenteral administration.

* * * * *